(12) United States Patent
Herold et al.

(10) Patent No.: US 7,612,088 B2
(45) Date of Patent: Nov. 3, 2009

(54) HETEROCYCLIC COMPOUNDS AND THEIR USE AS ALDOSTERONE SYNTHASE INHIBITORS

(75) Inventors: Peter Herold, Basel (CH); Robert Mah, Muttenz (CH); Vincenzo Tschinke, Binningen (CH); Christoph Schumacher, Bettingen (CH); Michael Quirmbach, Basel (CH)

(73) Assignee: Speedel Experimenta AG, Allschwil (CH)

( * ) Notice: Subject to any disclaimer, the term of this patent is extended or adjusted under 35 U.S.C. 154(b) by 116 days.

(21) Appl. No.: 11/597,620

(22) PCT Filed: May 27, 2005

(86) PCT No.: PCT/EP2005/052417

§ 371 (c)(1),
(2), (4) Date: Nov. 27, 2006

(87) PCT Pub. No.: WO2005/118557

PCT Pub. Date: Dec. 15, 2005

(65) Prior Publication Data

US 2007/0208035 A1    Sep. 6, 2007
US 2008/0318978 A2   Dec. 25, 2008

(30) Foreign Application Priority Data

May 28, 2004   (CH) .................................. 0916/04

(51) Int. Cl.
  *A61K 31/437*   (2006.01)
(52) U.S. Cl. ........................................ 514/300; 546/121
(58) Field of Classification Search .................. 546/121
  See application file for complete search history.

(56) References Cited

U.S. PATENT DOCUMENTS 4,824,846 A    4/1989   Kampe et al.
5,057,521 A    10/1991  Häusler et al.

FOREIGN PATENT DOCUMENTS

| DE | 36 09 596 | 10/1987 |
|----|-----------|---------|
| EP | 0 356 673 | 3/1990  |
| EP | 0 366 609 | 5/1990  |
| EP | 0 426 225 | 5/1991  |
| JP | 9-71586   | 3/1997  |
| WO | 93/15079  | 8/1993  |

OTHER PUBLICATIONS

Database Crossfire Beilstein, Beilstein Institut Zur Foederung Der Chemischen Wissenchaften, Frankfurt, AM Main, DE; Database-accession No. 958161, (BRN), XP002355985 & Angew. Chem., vol. 83, pp. 287-288, 1971.
Database CA 'Online!, Chemical Abstracts Service, Columbus, Ohio, US; Kashima, Minoru et al., "Antithrombotic agents . . . ", XP002355993, retrieved from CHEMABS, Databse accession No. 139:41766 abstract & JP 2003 171294 A, Jun. 17, 2003.

*Primary Examiner*—James O Wilson
*Assistant Examiner*—Brian McDowell
(74) *Attorney, Agent, or Firm*—Wenderoth, Lind & Ponack, L.L.P.

(57) ABSTRACT

The application relates to novel heterocyclic compounds of the general formula (I) in which R, $R^1$, $R^2$, W, X, Y, Z and n have the meanings defined in the description, to a process for their preparation and to the use of these compounds as medicaments, in particular as aldosterone synthase inhibitors.

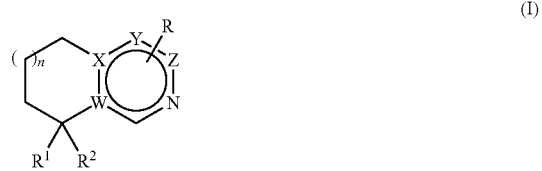

11 Claims, No Drawings

HETEROCYCLIC COMPOUNDS AND THEIR USE AS ALDOSTERONE SYNTHASE INHIBITORS

The invention relates to novel heterocycles, to a process for preparing the compounds of the invention, to pharmaceutical products containing them, and to their use as active pharmaceutical ingredients, in particular as aldosterone synthase inhibitors.

The present invention relates firstly to compounds of the general formula

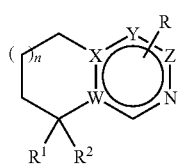

in which
W is C or, if Z is a bond and X is C, is also N;
X is C or, if Z is a bond, is also N;
Y is C or, if Z is C, is also N;
Z is C or a bond;
R a) is hydrogen; or
b) is $C_1$-$C_8$-alkyl, $C_1$-$C_8$-alkoxy, halogen or trifluoromethyl;
$R^1$ a) is $C_3$-$C_8$-cycloalkyl-$C_0$-$C_4$-alkyl or heterocyclyl-$C_0$-$C_4$-alkyl, where the heterocyclyl radical is at least partially saturated and the radicals are unsubstituted or substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulfonyl, aryl-$C_0$-$C_4$-alkoxycarbonyl, aryl, cyano, halogen, unsaturated heterocyclyl, oxo, trifluoromethoxy, trifluoromethyl or tri-$C_1$-$C_4$-alkylsilyl; or
b), if W is N, is also $C_1$-$C_8$-alkyl, $C_2$-$C_8$-alkenyl or $C_2$-$C_8$-alkynyl;
$R^2$ a) is hydrogen; or
b) is $C_1$-$C_8$-alkyl, $C_0$-$C_8$-alkylcarbonyl, $C_3$-$C_8$-cycloalkyl-$C_0$-$C_4$-alkyl or heterocyclyl-$C_0$-$C_4$-alkyl, where the heterocyclyl radical is at least partially saturated and the radicals are unsubstituted or substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulfonyl, aryl-$C_0$-$C_4$-alkoxycarbonyl, aryl, cyano, halogen, unsaturated heterocyclyl, oxo, trifluoromethoxy, trifluoromethyl or tri-$C_1$-$C_4$-alkylsilyl;
n is 0-2;
and the salts thereof, preferably the pharmaceutically usable salts thereof.
where, if W, X, Y and Z are C, $R^1$ is not an $C_1$-$C_8$-alkyl substituted piperazinyl radical.

The term aryl stands for an aromatic hydrocarbon radical which generally comprises 5-14, preferably 6-10, carbon atoms and is, for example, phenyl, indenyl, e.g. 2- or 4-indenyl, or naphthyl, e.g. 1- or 2-naphthyl. Aryl having 6-10 carbon atoms is preferred, especially phenyl or 1- or 2-naphthyl. Said radicals may be unsubstituted or substituted one or more times, e.g. once or twice, it being possible for the substituent to be in any position, e.g. in the o, m or p position of the phenyl radical or in the 3 or 4 position of the 1- or 2-naphthyl radical, and it also being possible for a plurality of identical or different substituents to be present.

Aryl-$C_0$-$C_4$-alkyl is, for example, phenyl, naphthyl or benzyl.

The term heterocyclyl stands for a saturated, partially saturated or unsaturated, 4-8-membered, particularly preferably 5-membered, monocyclic ring system, for a saturated, partially saturated or unsaturated, 7-12-membered, particularly preferably 9-membered, bicyclic ring system and also for a saturated, partially saturated or unsaturated, 7-12-membered tricyclic ring system, in each case comprising an N, O or S atom in at least one ring, it also being possible for an additional N, O or S atom to be present in one ring. Said radicals may be unsubstituted or substituted one or more times, e.g. once or twice, it also being possible for a plurality of identical or different substituents to be present.

Unsaturated monocyclic heterocyclyl-$C_0$-$C_4$-alkyl is, for example, pyrrole, thiophene, thiazole or oxazole.

An example of saturated monocyclic heterocyclyl-$C_0$-$C_4$-alkyl is pyrrolidinyl or tetrahydrofuranyl.

Unsaturated bicyclic heterocyclyl-$C_0$-$C_4$-alkyl is for example benzofuranyl, benzothiophenyl, indazolyl, indolyl, isoquinolinyl or quinolinyl.

Partially saturated bicyclic heterocyclyl-$C_0$-$C_4$-alkyl is for example 4,5,6,7-tetrahydrobenzofuranyl or 4,5,6,7-tetrahydrobenzothiazolyl.

$C_3$-$C_8$-Cycloalkyl-$C_0$-$C_4$-alkyl is preferably 3-, 5- or 6-membered cycloalkyl-$C_0$-$C_4$-alkyl such as cyclopropyl, cyclopentyl or cyclohexyl.

$C_1$-$C_8$-Alkyl may be straight-chain or branched and/or bridged and is, for example, methyl, ethyl, propyl, isopropyl, butyl, isobutyl, secondary butyl, tertiary butyl, or a pentyl, hexyl or heptyl group.

$C_2$-$C_8$-Alkenyl is, for example, ethenyl, propenyl, isopropenyl, butenyl, isobutenyl, secondary butenyl, tertiary butenyl, or a pentenyl, hexenyl or heptenyl group.

$C_2$-$C_8$-Alkynyl is, for example, ethynyl, propynyl, butynyl, or a pentynyl, hexynyl or heptynyl group.

$C_1$-$C_8$-Alkoxy is, for example, $C_1$-$C_5$-alkoxy such as methoxy, ethoxy, propyloxy, isopropyloxy, butyloxy, isobutyloxy, secondary butyloxy, tertiary butyloxy or pentyloxy, but may also be a hexyloxy or heptyloxy group.

$C_1$-$C_8$-Alkylcarbonyl is preferably $C_1$-$C_5$-alkoxycarbonyl such as methoxycarbonyl, ethoxycarbonyl, propyloxycarbonyl, isopropyloxycarbonyl, butyloxycarbonyl, isobutyloxycarbonyl, secondary butyloxycarbonyl or tertiary butyloxycarbonyl.

$C_0$-$C_8$-Alkylcarbonyl is, for example, formyl, acetyl, propionyl, propylcarbonyl, isopropylcarbonyl, butylcarbonyl, isobutylcarbonyl, secondary butylcarbonyl or tertiary butylcarbonyl.

Halogen is, for example, fluorine, chlorine, bromine or iodine.

The compound groups mentioned below are not to be regarded as closed; on the contrary, parts of these compound groups may be replaced by one another or by the definitions given above, or be omitted, in a meaningful way, e.g. to replace general by more specific definitions.

Preferred compounds of the formula (I) are compounds of the general formulae

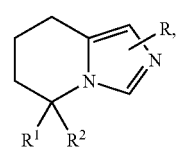

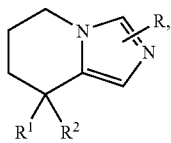 (Ib)

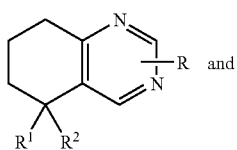 (Ic)

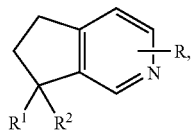 (Id)

where the meanings of the substituents R, $R^1$ and $R^2$ are as indicated for compounds of the formula (I).

R is preferably hydrogen or $C_1$-$C_8$-alkyl, particularly preferably hydrogen or methyl.

$R^1$ is preferably $C_3$-$C_8$-cycloalkyl-$C_0$-$C_4$-alkyl or heterocyclyl, very particularly preferably optionally monosubstituted cyclohexyl, pyrrolidinyl, 4,5,6,7-tetrahydroisobenzofuranyl or 4,5,6,7-tetrahydrobenzothiazolyl.

$R^2$ is preferably hydrogen, halogen, $C_1$-$C_8$-alkyl or $C_0$-$C_8$-alkylcarbonyl.

n is preferably a number 0 to 1.

Preferred substituents for $C_3$-$C_8$-cycloalkyl-$C_0$-$C_4$-alkyl or heterocyclyl are halogen, cyano, trifluoromethyl, heterocyclyl or $C_0$-$C_8$-alkylcarbonyl. Very particularly preferred substituents for $C_3$-$C_8$-cycloalkyl-$C_0$-$C_4$-alkyl or heterocyclyl are fluorine, bromine, chlorine, cyano, thiophenyl, thiazolyl, oxazolyl or acetyl.

The compounds of the formula (I) which have at least one asymmetric carbon atom can exist in the form of optically pure enantiomers, mixtures of enantiomers or as racemates. Compounds having a second asymmetric carbon atom can exist in the form of optically pure diastereomers, mixtures of diastereomers, diastereomeric racemates, mixtures of diastereomeric racemates or as meso compounds. The invention includes all these forms. Mixtures of enantiomers, racemates, mixtures of diastereomers, diastereomeric racemates or mixtures of diastereomeric racemates can be fractionated by conventional methods, e.g. by racemate resolution, column chromatography, thin-layer chromatography, HPLC and the like.

The term "pharmaceutically usable salts" includes salts with inorganic or organic acids, such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like. Salts of compounds having salt-forming groups are, in particular, acid addition salts, salts with bases or, if a plurality of salt-forming groups is present, optionally also mixed salts or inner salts.

The compounds of the formula (I) can be prepared in a manner analogous to preparation processes disclosed in the literature. Details of the specific preparation variants can be found in the examples.

The compounds of the formula (I) can also be prepared in optically pure form. Separation into antipodes is possible by methods known per se, either preferably at an early stage of the synthesis by salt formation with an optically active acid such as, for example, (+)- or (−)-mandelic acid and separation of the diastereomeric salts by fractional crystallization or preferably by derivatization with a chiral auxiliary component such as, for example, (+)- or (−)-camphanyl chloride, and separation of the diastereomeric products by chromatography and/or crystallization and subsequent cleavage of the linkage to the chiral auxiliary. The pure diastereomeric salts and derivatives can be analyzed to determine the absolute configuration of the contained compound using conventional spectroscopic methods, a particularly suitable method being single-crystal X-ray spectroscopy.

Salts are primarily the pharmaceutically usable or nontoxic salts of compounds of the formula (I). Such salts are formed for example by compounds of the formula (I) having an acidic group, e.g. a carboxy or sulpho group, and are, for example, salts thereof with suitable bases, such as nontoxic metal salts derived from metals of group Ia, Ib, IIa and IIb of the Periodic Table of Elements, e.g. alkali metal, in particular lithium, sodium or potassium salts, alkaline earth metal salts, for example magnesium or calcium salts, also zinc salts or ammonium salts, and those salts formed with organic amines such as optionally hydroxy-substituted mono-, di- or trialkylamines, in particular mono-, di- or tri-lower-alkylamines, or with quaternary ammonium bases, e.g. methyl-, ethyl-, diethyl- or triethylamine, mono-, bis- or tris(2-hydroxy-lower-alkyl)amines such as ethanol-, diethanol- or triethanolamine, tris(hydroxymethyl)methylamine or 2-hydroxy-tertiary-butylamine, N,N-di-lower-alkyl-N-(hydroxy-lower-alkyl)amine, such as N,N-dimethyl-N-(2-hydroxyethyl) amine, or N-methyl-D-glucamine, or quaternary ammonium hydroxides such as tetrabutylammonium hydroxide. The compounds of the formula (I) having a basic group, e.g. an amino group, can form acid addition salts, e.g. with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, also amino acids such as, for example, the above-mentioned α-amino acids, and methanesulphonic acid, ethanesulphonic acid, 2-hyroxyethanesulphonic acid, ethane-1,2-disulphonic acid, benzenesulphonic acid, 4-toluenesulphonic acid, naphthalene-2-sulphonic acid, 2 or 3-phosphoglycerate, glucose 6-phosphate, N-cyclohexylsulphamic acid (to form cyclamates) or with other acidic organic compounds such as ascorbic acids. Compounds of the formula (I) having acidic and basic groups can also form inner salts.

Pharmaceutically unsuitable salts can also be used for isolation and purification.

The compounds of the formula (I) also include compounds in which one or more atoms are replaced by their stable, nonradioactive isotopes; for example a hydrogen atom by deuterium.

Prodrug derivatives of the compounds described above are derivatives thereof which on use in vivo release the original compound through a chemical or physiological process. A prodrug may be converted into the original compound for example when a physiological pH is reached or by enzymatic conversion. Examples of possible prodrug derivatives are esters of freely available carboxylic acids, S- and O-acyl derivatives of thiols, alcohols or phenols, where the acyl group is as defined above. Preference is given to pharmaceutically usable ester derivatives which are converted by solvolysis in physiological medium into the original caroxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxy, lower alkoycarbonyl)-alkyl esters or such as lower α-(alkanoyloxy, alkoxycarbonyl or dialkylaminocarbonyl)-alkyl esters; pivaloyloxymethyl esters and similar esters are conventionally used as such.

Because of the close relationship between a free compound, a prodrug derivative and a salt compound, a defined compound in this invention also includes its prodrug derivative and salt form where this is possible and appropriate.

Aldosterone is a steroidal hormone which is synthesized in the zona glomerulosa cells of the adrenal cortex by the enzyme aldosterone synthase (CYP11B2). Aldosterone production and secretion is controlled by the adrenocorticotropic hormone (ACTH), angiotensin II, potassium and sodium ions. The primary biological function of aldosterone is to regulate the salt balance, since aldosterone controls the reabsorption of sodium ions from the renal filtrate and the secretion of potassium ions into the renal filtrate. The state of excessive aldosterone secretion, also called hyperaldosteronism, may lead to high blood pressure, hypokalaemia, alkalosis, muscle weakness, polyuria, polydipsia, oedemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The described compounds can be employed for the prevention, for delaying the progression, or for the treatment of states such as hypokalaemia, hypertension, congestive heart failure, acute and, in particular, chronic renal failure, cardiovascular restenosis, atherosclerosis, metabolic syndrome (syndrome X), adiposity (obesity), vasculitis, primary and secondary hyperaldosteronism, proteinuria, nephropathy, diabetic complications such as diabetic nephropathy, myocardial infarction, coronary heart disease, increased collagen formation, fibrosis, vascular and coronary tissue changes (remodelling) secondary to hypertension, endothelial dysfunction and oedemas secondary to cirrhosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is controlled by ACTH. The primary biological function of cortisol is to regulate the production and the availability of carbohydrates for the brain and other metabolically active tissues. Increased cortisol production and secretion is a normal physiological response to stress and leads to the essential mobilization of fats, proteins and carbohydrates to meet an increased demand for energy by the body. Chronically excessive cortisol release describes the condition of Cushing's syndrome. Cushing's syndrome may be produced on the one hand by hypersynthesis of cortisol, which may be generated by an adrenocortical tumour, or be produced on the other hand as the consequence of excessive stimulation of the adrenal cortex by ACTH. The first form is referred to as primary hypercortisolism, and the second form as secondary hypercortisolism. An excessive and persistent cortisol secretion may also accompany a stress response, which may lead to depression, hyperglycemia and to suppression of the immune system.

The chemical compounds described in this invention inhibit the enzyme 11-β-hydroxylase (CYP11B1) and can therefore, due to the inhibition of cortisol synthesis, be employed for the prevention, delaying the progression or treatment of Cushing's syndrome and of the physical and mental consequences of excessive and persistent cortisol secretion in states of stress. Therefore, these compounds may be useful for the treatment and prevention of conditions such as the ectopic adrenocorticotropic (ACTH) hormone syndrome, adrenal incidentaloma, primary pigmented nodular adrenocortical disease (PPNAD) and Carney complex (CNC), anorexia nervosa, chronic alcohol abuse, cigarette smoking, nicotine and cocaine withdrawal, post-traumatic stress disorder, cognitive dysfunction after stroke and cortisol-mediated mineralcorticoid excess.

Inhibition of aldosterone synthase (Cyp11B2) and of 11-β-hydroxylase (Cyp11B1) and of aromatase (Cyp19), by the compounds described above can be determined by the following in vitro assay:

The cell line NCI-H295R was originally isolated from an adrenocortical carcinoma and has been characterized in the literature through the stimulative secretion of steroid hormones and the presence of the key enzymes necessary for steroidogenesis. These include Cyp11A (cholesterol side-chain cleavage), Cyp11B1 (steroid 11β-hydroxylase), Cyp11B2 (aldosterone synthetase), Cyp17 (steroid 17α-hydroxylase and/or 17,20 lyase), Cyp19 (aromatase), Cyp21B2 (steroid 21-hydroxylase) and 3β-HSD (hydroxysteroid dehydrogenase). The cells have the physiological characteristics of zonally undifferentiated human fetal adrenal cells, with the ability to produce the steroid hormones of each of the three phenotypically distinct zones found in the adult adrenal cortex.

The NCI-295R cells (American Type Culture Collection, ATCC, Rockville, Md., USA) are cultured in Dulbecco's Modified Eagle'Ham F-12 medium (DME/F12) that is supplemented with Ultroser SF serum (Soprachem, Cergy-Saint-Christophe, France) as well as insulin, transferring, selenit (I-T-S, Becton Dickinson Biosiences, Franklin Lakes, N.J., USA) and antibiotics in 75 $cm^2$ cell culture flasks at a temperature of 37° C. and a 95% air/5% CO2 humidified atmosphere. The cells are subsequently transferred in a 24-well plate and seeded in presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence or absence of cell stimulatory agents. The test compound is added in a concentration range of 0.2 nanomolar to 2 millimolar. Angiotensin-II (at 10 or 100 nanomolar concentration), potassium ions (at 16 millimolar), forskolin (at 10 micromolar) or a combination of two agents may serve as cell-stimulatory agent. The cellular secretion of aldosterone, cortisol, corticosterone and estradiol/estrone into the cell culture medium can be quantitatively assessed with commercially available immuno-assays and specific monoclonal antibodies according to the manufacturer's instructions.

The degree of secretion of a selective steroid is used as a measure of enzyme activity, respectively enzyme inhibition in the presence of absence of a test compound. The dose-dependent enzyme inhibitory activity of a compound is reflected in a inhibition curve that is characterized by an IC50 value. The IC50 values for active test compounds are generated by simple linear regression analysis to establish inhibition curves without data weighing. The inhibition curve is generated by fitting a 4-parameter logistic function to the raw data of the samples using the least squares approach. The function is described as follows:

$$Y=(d-a)/((1+(x/c)^{-b}))+a$$

with:
 a=minimum
 b=slope
 c=IC50
 d=maximum
 x=inhibitor concentrations

The compounds of the present invention show inhibitory effects in in vitro systems with minimal concentrations of about $10^{-3}$ to about $10^{-10}$ mol/l.

The aldosterone-reducing effect of the compounds described herein can be tested in vivo by the following protocol:

Adult male Sprague Dawley rats, weighing between 125 and 150 grams, are kept, housed singly, under the usual conditions of light and temperature. At 16.00 h on the first day of the experiment, the animals receive a subcutaneous injection of the depot ACTH product in a dose of 1.0 mg/kg of weight (SYNACTEN-Depot Novartis, Basel, CH). Pilot studies showed that this ACTH dose increased plasma aldosterone and corticosterone significantly by 15-fold and 25-fold respectively over a period of at least 18 hours. At 8.00 h in the morning of the second day, the animals, divided into test groups of 5 animals, receive administration either of water orally or of a compound in a variable dose range of 0.01-10 mg/kg orally by gavage. Two hours later, blood is taken in EDTA-treated Eppendorf vessels. Plasma samples are obtained by centrifugation of the blood and can be stored at −20° C. An alternative method to stimulate the aldosterone secretion consists in subjecting adult male catherized Wistar rats of 250 to 350 grams weight for 48 hours to a low salt diet and 16 hours prior the start of the experiment with an subcutaneous or intraperitoneal application of furosemide at 10 mg/kg. The furosemide application may be repeated 2 hours prior to the start of the experiment. Pilot studies indicated that this treatment results in a 5 to 20 fold increase in plasma aldosterone levels over a period of 12 to 24 hours. The catheters are chronically implanted in the carotid of the animals and allow thus the periodical sampling of up to 0.2 ml of blood using an AccuSampler (DiLab Europe, Lund, Sweden). The experiment starts with the oral administration of test compound in a dose range of 0.01 to 10 mg/kg. The blood sampling with the AccuSampler occurs 1 hour before the administration of test compound and 2, 4, 6, 8, 12, 16 and 24 hours thereafter. The blood samples are anticoagulated with heparin and centrifuged.

The plasma samples derived form both protocols are tested for the steroid content in previously described radioimmunoassays. The reduction in the steroid levels, such as, for example, aldosterone, serves as a measure of the in vivo bioavailability and enzyme inhibiting activity of the compounds described herein.

The reduction of cardiac damage upon inhibition of the aldosterone synthase with the herein described compounds may be evaluated with the following protocol. The protocol corresponds largely to the protocol described in the publication by Rocha et al. (Endocrinology, Vol. 141, pp 3871-3878, 2000). Adult male Wistar rats are housed in individual cages and given 0.9% saline as drinking fluid ad libitum throughout the experiment. Three days later, rats are placed on one of the three dosing protocols. Group I (control group with 8 animals) receives for 14 days the nitric oxide synthase inhibiting agent L-NAME (N-nitro-L-arginine methylester, SIGMA, St. Louis, Mo., USA). On day 11 of L-NAME treatment, an osmotic minipump containing only saline is implanted in each animal subcutaneously. Group II (L-NAME/Ang II with 8 animals) receives L_NAME For 14 days, and on day 11 of L-NAME treatment, an osmotic minipump containing Ang II is implanted in each animal subcutaneaously. Group III (L-NAME/Ang II/test compound with 8 animals) is treated similarly to group II but receives test compound in a daily dose range of 0.2 to 10 mg/kg rat weight. The test compound is dissolved in distilled water and given by oral gavage; whereas groups I and II receive the vehicle without test compound. The experiment is concluded on day 14 of L-NAME treatment. L-NAME is administered in 0.9% saline containing drinking water at a concentration of 60 mg/100 ml which results in a daily intake of approximately 60 mg/kg. Angioensin II is administered via Alzet osmotic mini pumps (model 2001, Alza Corp, Palo Alto, Calif., USA). The minipimp is implanted subcutaneously at the nape of the neck. Angiotensin II (human, 99% peptide purity) is purchased from Sigma Chemical Corp., St Louis, Mo., USA and administered at a dose of 225 ug/kg/day in saline. The concentration of angiotensin II used to fill the pumps is calculated based upon: a) the mean pump rate provided by the manufacturer; b) the body weight of the animals on the day before implantation of the pumps and c) the planned dose. The rats are sacrificed on day 14. Their hearts are removed and sliced through the ventricle/atrium in a "bread-loaf" manner, yielding three samples from the following gross cardiac regions: superior, middle and inferior. The samples are fixed in 10% buffered formalin. Paraffin sections are cut and stained with hematoxyliin/eosin. A single investigator who is blinded to the experimental groups views slides. One slide from each of the three gross cardiac sample regions is analyzed per rat. Cardiac sites (left and right ventricles and the septum) are evaluated separately. The entire section is assessed histologically for the presence of myocardial damage (regardless of the severity) as evidenced by the presence of my necrosis, inflammatory cells, hemorrhages and general tissue disruption. Evaluation of the histological data is made by comparing groups II and III, i.e. Angiotensin II with or without test compound. The evaluation of the samples may occur semiquantitatively and can be illustrated with a score table.

The lowering of blood pressure and the reduction of cardiac damage and nephropathy upon inhibition of the aldosterone synthase with the herein described compounds may be evaluated with following protocol. The experiments occur in 4 week old male double transgenic rats (dTGR) that overexpress human angiotensinogen as well as human renin and therefore develop hypertension. Age-paired Sprague-Dawley (SD) rats serve as non-hypertensive control animals. The animals are separated in test groups that receive either test compound or vehicle (control group) for 3-4 weeks. The animals are fed standard chow and get drinking water ad libitum during the whole experiment. The systolic and diastolic blood pressure as well as the heart rate are monitored with implanted telemetric transducers whereby the animals are free and unrestricted to move. The rats are transferred once a week or 24 hours into a metabolic cage in order to measure the 24 hour urinary albumin excretion. The dimensions of the heart (left ventricular mass, end-diastolic diameter and wall thickness, thickness of the septum, shortening fraction) and the diastolic filling are determined by echocardiography at the beginning and the end of the treatment under isofluran anesthesia (M-mode monitoring in the short axis and tissue Doppler representation using a commercial echocardiogram instrument that is equipped with a 15 MHz probe). The animals are sacrificed at the end of the study and the kidneys and heart removed for weighing and immunohistochemical assessment (fibrosis, macrophage/T-cell infiltration, etc.).

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally in tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures permanent release of the compound. The amount of substance to be administered can vary over a wide range and represent every effective dose. Depending on the patient to be treated or the condition to be treated and mode of administration, the dose of the e substance each day can be between about 0.005 and 5 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatin capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatin, disintegrants such as potato starch or crosslinked polyvinylpyrrolidone (PVPP) and lubricants such as stearic acid or magnesium stearate.

Examples of excipients suitable for soft gelatin capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semiliquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, welting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

as therapeutic combination in the form of a product or of a kit which is composed of individual components consisting of a compound described herein, in free form or as pharmaceutically usable salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.

as method for combined use, such as, for example, in simultaneous or sequential succession, of a therapeutically effective amount of a compound described herein, in free or in pharmaceutically usable salt form, and of a second active ingredient with blood pressure-lowering, inotropic, antidiabetic, obesity-reducing or lipid-lowering effect.

The compounds described herein and their pharmaceutically usable salts can be used in combination with (i) one or more blood pressure-lowering active ingredients, as such for example:

renin inhibitors such as aliskiren;

angiotensin II receptor blockers such as candesartan, irbesartan, olmesartan, losartan, valsartan, telmisartan etc.;

ACE inhibitors such as quinapril, ramipril, trandolapril, lisinopril, captopril, enalapril etc.;

calcium antagonists such as nifedipine, nicardipine, verapamil, isradipine, nimodipine, amlodipine, felodipine, nisoldipine, diltiazem, fendiline, flunarizine, perhexiline, gallopamil etc.;

diuretics such as hydrochlorthiazide, chlorothiazide, acetazolamide, amiloride, bumetanide, benzthiazide, etacrynic acid, furosemide, indacrinone, metolazone, triamterene, chlortalidone, etc.;

aldosterone receptor blockers such as spironolactone, eplerenone;

endothelin receptor blockers such as bosentan;

phosphodiesterase inhibitors such as amrinone, sildenafil;

direct vasodilators such as dihydralazine, minoxidil, pinacidil, diazoxide, nitroprusside, flosequinan etc., α- and β-receptor blockers such as phentolamine, phenoxybenzamine, prazosin, doxazosin, terazosin, carvedilol, atenolol, metoprolol, nadolol, propranolol, timolol, carteolol etc.;

neutral endopeptidase (NEP) inhibitors;

sympatholytics such as methyldopa, clonidine, guanabenz reserpine (ii) one or more agents having inotropic activity, as such for example:

cardiac glycosides such as digoxin;

β-receptor stimulators such as dobutamine thyroid hormone such as thyroxine (iii) one or more agents having antidiabetic activity, as such for example:
- insulins such as insulin aspart, insulin human, insulin lispro, insulin glargine and further fast-, medium- and long-acting insulin derivatives and combinations
- insulin sensitizers such as rosiglitazone, pioglitazone;
- sulphoicnylureas such as glimepiride, chlorpropamide, glipizide, glyburide etc.;
- biguanides such as metformin;
- glucosidase inhibitors such as acarbose, miglitol;
- meglitinides such as repaglinide, nateglinide;

(iv) one or more obesity-reducing ingredients, as such for example:
- lipase inhibitors such as orlistate;
- appetite suppressants such as sibutramine, phentermine;

(v) one or more lipid-lowering active ingredients, such as, for example,
- HMG-CoA reductase inhibitors such as lovastatin, fluvastatin, pravastatin, atorvastatin, simvastatin, rosuvastatin etc.;
- fibrate derivatives such as fenofibrate, gemfibrozil etc.;
- bile acid-binding active ingredients such as colestipol, colestyramine, colesevelam
- cholesterol absorption inhibitors such as ezetimibe
- nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The presently described compounds and the pharmaceutically usable salts thereof may find use as combinations with
(i) a diagnostic test system, that allows the quantitative determination of the plasma renin concentration (PRC)
(ii) a diagnostic test system, that allows the quantitative determination of the plasma aldosterone concentration (PAC)
(iii) a diagnostic test system, that allows the quantitative determination of the plasma renin activity (PRA)
(iv) a diagnostic test system, that allows the quantitative determination of the plasma aldosterone to renin concentration ratio (ARC)
(v) a diagnostic test system, that allows the quantitative determination of the plasma aldosterone to renin activity ratio (ARR)
(vi) a diagnostic test system, that allows the quantitative determination of the plasma cortisol concentration (PCC)

Such combination of a diagnostic test system and a therapy may be used separately or in preparation with individual components.

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The ratio amounts of solvents to one another is always stated in proportions by volume. Chemical names of final products and intermediates were generated with the aid of the AutoNom 2000 (Automatic Nomenclature) program.

HPLC gradients on Hypersil BDS C-18 (5 µm); column: 4×125 mm:

95% water*/5% acetonitrile* to 0% water*/100% acetonitrile* in 10 minutes+2 minutes (1 ml/min)
* contains 0.1% trifluoroacetic acid The following abbreviations are used:
RF ratio of the distance migrated by a substance to the distance of the solvent from the starting point in thin-layer chromatography
Rt retention time of a substance in HPLC (in minutes)
m.p. melting point (temperature)

EXAMPLE 1

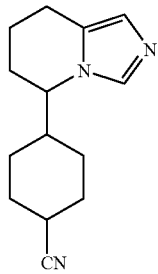

4-(5,6,7,8-Tetrahydroimidazo[1,5-a]phyridin-5-yl) cyclohexanecarbonitrile

A solution of 0.56 g of N-tert-butyl-4-(5,6,7,8-tetrahydroimidazo[1,5-a]pyridin-5-yl)-cyclohexanecarboxamide and 1 ml of thionyl chloride in 30 ml of chloroform is stirred under reflux for 6 hours. The reaction mixture is cooled to room temperature and evaporated. The residue is taken up in dichloromethane and mix with saturated aqueous sodium bicarbonate solution. The organic phase is separated off, and the aqueous phase is extracted with dichloromethane (2×). The combined organic phases are dried with sodium sulphate and evaporated. The title compound is obtained as a yellow oil from residue by flash chromatography (SiO$_2$ 60F). Rf=0.45 (dichloromethane:methanol=95:5); Rt=4.66.

The starting materials are prepared as follows:

a) N-tert-Butyl-4-(5,6,7,8-tetrahydroimidazo[1,5-a] pyridin-5-yl)cyclohexanecarboxamide A solution of 0.56 g of 4-(5,6,7,8-tetrahydroimidazo[1,5-a]pyridin-5-yl)cyclohexanecarboxylic acid and 7.5 ml of thionyl chloride is stirred under reflux for 30 minutes. The reaction mixture is cooled to room temperature and evaporated. The residue is dissolved in dichloromethane, cooled to 0° C., and then 2 ml of tert-butylamine are added, and the reaction mixture is subsequently stirred for a further 15 hours. The reaction mixture is diluted with dichloromethane and mixed with saturated aqueous sodium bicarbonate solution. The organic phase is separated off and the aqueous phase is extracted with dichloromethane (2×). The combined organic phases are dried with sodium sulphate and evaporated. The title compound is obtained from the residue by flash chromatography (SiO$_2$ 60F).

b) 4-(5,6,7,8-Tetrahydroimidazo[1,5-a]pyridin-5-yl) cyclohexanecarboxylic acid A solution of 1.5 g of 4-(5,6,7,8-tetrahydroimidazo[1,5-a] pyridin-5-yl)benzoic acid [93178-73-5] in 5 ml of acetic acid is hydrogenated (50 bar) in the presence 0.05 g of Nishimura catalyst at room temperature. The reaction mixture is clarified by filtration, and the filtrate is evaporated. The crude title compound is obtained from the residue.

EXAMPLE 2

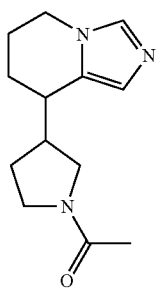

1-[3-(5,6,7,8-Tetrahydroimidazo[1,5-a]pyridin-8-yl) pyrrolidin-1-yl]ethanone 0.15 ml of acetyl chloride is added dropwise to a solution of 0.38 g 8-pyrrolidin-3-yl-5,6,7,8-tetrahydroimidazo[1,5-a] pyridine, 0.16 ml of pyridine and 2 ml of chloroform at 0° C., and the mixture is then warmed to room temperature. After 18 hours, water is added to the reaction mixture, and it is extracted with ethyl acetate (3×)—the combined organic phases are dried with sodium sulphate and evaporate. The title compound is identified from the residue by flash chromatography (SiO$_2$ 60F) on the basis of the Rf.

The starting materials are prepared as follows:

a) 8-Pyrrolidin-3-yl-5,6,7,8-tetrahydroimidazo[1,5-a] pyridine 0.14 ml of conc. H$_2$SO$_4$ are added dropwise to a suspension of 0.19 g of lithiumaluminium hydride and 10 ml of terahydrofuran at 0° C. After stirring for 30 minutes a solution of 0.41 g of 3-(5,6,7,8-tetrahydroimidazo[1,5-a]pyridin-8-yl) pyrrolidin-2-one and 10 ml of tetrahydrofuran is added dropwise, and the mixture is then warmed to room temperature. After 1 hour, the reaction mixture is cooled to 0° C. and quenched successively with 1 ml of tetrahydrofuran/water (1:1) and 3 ml of 5% NaOH. The precipitate is filtered off and washed with tetrahydrofuran (2×)—the combined organic phases are dried with sodium sulphate and evaporated. The crude title compound is obtained from the residue.

b) 3-(5,6,7,8-Tetrahydroimidazo[1,5-a]pyridin-8-yl) pyrrolidin-2-one

A solution of 0.41 g of 3-(6,7-dihydro-5H-imidazo[1,5] pyridin-8-ylidene)pyrrolidin-2-one and 10 ml of methanol is hydrogenated in the presence of 0.1 g of Pd(OH)$_2$/C 20% at room temperature. The reaction mixture is clarified by filtration, and the filtrate is evaporated. The title compound is identified from the residue by flash chromatography (SiO$_2$ 60F) on the basis of the Rf.

c) 3-(6,7-Dihydro-5H-imidazo[1,5-a]pyridin-8-ylidene)pyrrolidin-2-one 0.23 ml of phosphorus oxychloride are added dropwise to a solution of 0.50 g of 3-(8-hydro-5,6,7,8-tetrahydroimidazo [1,5-a]pyridin-8-yl)pyrrolidin-2-one and 7.5 ml of pyridine at 0° C., and the reaction mixture is then warmed to room temperature. After 1 hour, 1.02 ml of 1,8-diazabicyclo[5.4.0] undec-7-ene are added. After 3 hours water is added to the reaction mixture, and it is extra with dichloromethane (3×)—the combined organic phases are washed successively with 1N NaOH and water, dried with sodium sulphate and evaporated. The title compound is identified from the residue by flash chromatography (SiO$_2$ 60F) on the basis of the Rf.

d) 3-(8-Hydroxy-5,6,7,8-tetrahydroimidazo[1,5-a] pyridin-8-yl)pyrrolidin-2-one 1.25 ml of n-butyllithium (1.6M in hexane) are added dropwise to a solution to 0.29 ml of diisopropylamine and 2 ml of tetrahydrofuran at −78° C. After 30 minutes, a solution, cooled to −78° C., of 0.31 g of 1-trimethylsilanylpyrrolidin-2-one and 5 ml of tetrahydrofuran is added dropwise. The mixture is stirred for a further 30 minutes and then a solution of 0.27 g of 6,7-dihydro-5H-imidazo[1,5-a]pyridin-8-one [426219-51-4] and 5 ml tetrahydrofuran is added dropwise. The reaction mixture is stirred at −78° C. for 1 hour and then at 0° C. for 2 hours. The mixture is quenched with saturated aqueous ammonium chloride solution/water (1:1), the tetrahydrofuran is evaporated, and the residue is extracted with dichloromethane (3×). The combined organic phases are dried with sodium sulphate and evaporated. The title compound is identified from the residue by flash chromatography (SiO$_2$ 60F) on the basis of the Rf.

EXAMPLE 3

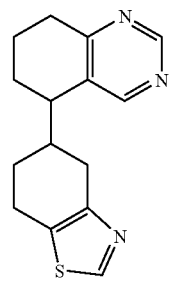

5-(4,5,6,7-Tetrahydrobenzothiazol-5-yl)-5,6,7,8-tetrahydroquinazoline

A solution of 0.27 g of 5-(6,7-dihydro-4H-benzothiazol-5-ylidene)-5,6,7,8-tetahydro-quinazoline, 15 ml of ethanol and 4 ml conc. HCl is hydrogenated in the presence of 0.5 g of Pd/C 10% at room temperature for 4 hours. The reaction mixture is clarified by filtration, and the filtrate is evaporated. The title compound is identified from the residue by flash chromatography (SiO$_2$ 60F) on the basis of the Rf.

The starting materials are prepared as follows:

a) 5-(6,7-Dihydro-4H-benzothiazol-5-ylidene-5,6,7,8-tetrahydroquinazoline 1.06 g of benzenesulphonyl chloride is added to a solution of 0.66 g of 5-(5-hydroxy-5,6,7,8-tetrahydroquinazoline-5-yl)-4,5,6,7-tetrahydrobenzothiazole-5-carboxylic acid and 20 ml of pyridine at 0° C. After 2 hours at 0° C., the reaction mixture is poured into ice-water—the resulting solid is filtered off, dried, dissolved in 1 ml of 2,4,6-trimethylpyridine and then heated to 140° C. After 90 minutes, the reaction mixture is cooled to room temperature, mixed with hot water, stirred for 10 minutes and then the water is decanted off. This "water-treatment process" is repeated twice more. The solid is then dried and purified by flash chromatography (SiO$_2$ 60F). The title compound is identified on the basis of e Rf.

5-(5-Hydroxy-5,6,7,8-tetrahydroquinazolin-5-yl)-4,5,6,7-tetrahydrobenzothiazole-5-carboxylic acid 2.5 ml of n-butyllithium (1.6M in hexane) are added to a solution of 0.58 ml of diisopropylamine and 4 ml of tetrahydrofuran at −40° C. The mixture is warmed to −15° C. and then cooled again to −40° C. After this, a solution, cooled to −40° C., of 0.36 g of 4,5,6,7-tetrahydrobenzothiazole-5-carboxylic acid and 5 ml of tetrahydrofuran is added dropwise. The reaction mixture is warmed to 50° C., stirred for 2 hours, cooled to −40° C. and then a solution of 0.30 g of 7,8-dihydro-6H-quinazolin-5-one [21599-28-0] and 5 ml of tetrahydrofuran is added dropwise. The reaction mixture is stirred further at −40° C. for 2 hours and at room temperature for 16 hours, poured on ice and washed with diethyl ether (3×). The combined organic phases are extracted with water. The combined aqueous phases are acidified with 1N HCl and extracted with dichloromethane (2×)—the combined organic phases are washed with brine, dried with sodium sulphate and evaporated. The title compound is identified from the residue by flash chromatography (SiO$_2$ 60F) on the basis of the Rf.

c) 4,5,6,7-Tetrahydrobenzothiazole-5-carboxylic acid 6 ml of 2N NaOH are added to a solution of 0.42 g of ethyl 4,5,6,7-tetrahydrobenzothiazole-5-carboxylate [952203-30-8] and 24 ml of MeOH at room temperature. After 6 hours, the reaction mixture is evaporated. The residue is acidified with 4N HCl, diluted with water and extracted with ethyl acetate (2×)—the combined organic phases are dried with sodium sulphate and evaporated. The crude title compound is obtained from the residue.

The following compound is prepared in an analogous manner to the processes described in Example 3:

EXAMPLE 4 5-(4,5,6,7-Tetrahydrobenzothiazol-6-yl)-5,6,7,8-tetrahydroquinazoline starting from ethyl 4,5,6,7-tetrahydrobenzothiazole-6-carboxylate [7528-74-6]

The invention claimed is:

1. A compound of the formula

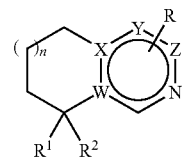

(I)

W is C, or if X is C, is also N;

X is C or N;

Y is C;

Z is a bond;

R a) is hydrogen; or b) is $C_1$-$C_8$-alkyl, $C_1$-$C_8$-alkoxy, halogen or trifluoromethyl;

$R^1$ is $C_3$-$C_8$-cycloalkyl-$C_0$-$C_4$-alkyl or a saturated, 4-8-membered, monocyclic heterocyclyl-$C_0$-$C_4$-alkyl, each of which is unsubstituted or substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulfonyl, aryl-$C_0$-$C_4$-alkoxycarbonyl, aryl, cyano, halogen, unsaturated heterocyclyl, oxo, trifluoromethoxy, trifluoromethyl or tri-$C_1$-$C_4$-alkylsilyl, wherein the heterocycle contains 1-3 heteroatoms selected from N, O, and S;

$R^2$ is hydrogen;

n is 0-2; or a pharmaceutically acceptable salt thereof.

2. The compound according to claim 1, characterized in that it corresponds to the formulae

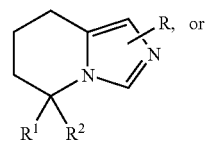

(Ia)

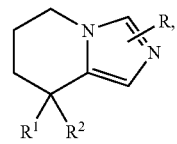

(Ib)

where the meanings of the substituents R, $R^1$ and $R^2$ are as indicated for compounds of the formula (I) according to claim 1.

3. The compound according to claim 1, where R is hydrogen or $C_1$-$C_8$-alkyl.

4. The compound according to claim 1, where n is a number 0 or 1.

5. The compound according to claim 2, where

R is hydrogen or $C_1$-$C_8$-alkyl;

$R^1$ is $C_3$-$C_8$-cycloalkyl-$C_0$-$C_4$-alkyl or heterocyclyl, in each case optionally substituted by halogen, cyano, trifluoromethyl, heterocyclyl or $C_0$-$C_8$-alkylcarbonyl; and $R^2$ is hydrogen.

6. A pharmaceutical product comprising a compound of the formula (I) according to claim 1, and conventional excipients.

7. The compound according to claim 2, where R is hydrogen or $C_1$-$C_8$-alkyl.

8. A pharmaceutical product comprising a compound of the formula (Ia), or (Ib) according to claim 2, and conventional excipients.

9. The compound according to claim 3, where R is hydrogen or methyl.

10. The compound according to claim 7, where R is hydrogen or methyl.

11. The compound according to claim 1, wherein the compound is:

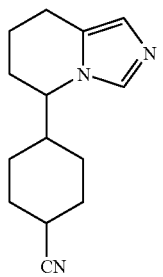 or 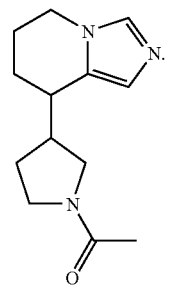

* * * * *